(12) United States Patent
Fisher et al.

(10) Patent No.: US 10,314,712 B2
(45) Date of Patent: Jun. 11, 2019

(54) TRANSCORTAL BONE JOINT FUSION SYSTEM

(71) Applicants: Jonathan Fisher, Sandpoint, ID (US); Andrew Lundquist, Edina, MN (US)

(72) Inventors: Jonathan Fisher, Sandpoint, ID (US); Andrew Lundquist, Edina, MN (US)

(*) Notice: Subject to any disclaimer, the term of this patent is extended or adjusted under 35 U.S.C. 154(b) by 4 days.

(21) Appl. No.: 14/954,737

(22) Filed: Nov. 30, 2015

(65) Prior Publication Data

US 2017/0151060 A1    Jun. 1, 2017

(51) Int. Cl.
| | | |
|---|---|---|
| *A61B 17/88* | (2006.01) | |
| *A61B 17/58* | (2006.01) | |
| *A61F 2/42* | (2006.01) | |
| *A61B 17/56* | (2006.01) | |

(52) U.S. Cl.
CPC ............ *A61F 2/4202* (2013.01); *A61B 17/56* (2013.01)

(58) Field of Classification Search
CPC .................. A61F 2/4202; A61F 2/4455; A61F 2002/3092; A61F 2002/4207; A61F 2002/4205; A61F 2002/30622; A61F 2002/3093; A61F 2/42; A61F 2/46; A61F 13/066
See application file for complete search history.

(56) References Cited

U.S. PATENT DOCUMENTS

| | | | |
|---|---|---|---|
| 8,585,744 B2 | 11/2013 | Duggal et al. | |
| 2009/0248084 A1* | 10/2009 | Hintermann | ....... A61B 17/8004 606/286 |
| 2011/0184413 A1 | 7/2011 | Slater | |
| 2012/0215223 A1* | 8/2012 | Chiodo | .............. A61B 17/8061 606/70 |
| 2013/0190827 A1* | 7/2013 | Butters | .............. A61B 17/8061 606/286 |
| 2014/0107798 A1 | 4/2014 | Jeng et al. | |
| 2014/0114313 A1 | 4/2014 | Early et al. | |

* cited by examiner

*Primary Examiner* — Ann Schillinger
(74) *Attorney, Agent, or Firm* — Wells St. John, P.S.

(57) ABSTRACT

Disclosed is a system and method for fusing two bones within a mammal. More particularly described is such a system and method for a transcortical fusion system wherein which a plate is affixed in a longitudinal slot or aperture cut into the anterior portion of the tibia and the talus, thereby achieving an fusion of the joint while placing the fusion site in the joint in compression.

7 Claims, 5 Drawing Sheets

TRANSCORTAL BONE JOINT FUSION SYSTEM

CROSS REFERENCE TO RELATED APPLICATION

This application does not claim the benefit of any other patent application.

TECHNICAL FIELD

This invention pertains to a system for fusing two bones within a mammal. More particularly described as one of multiple applications or embodiments is a transcortical ankle fusion system wherein a plate is affixed in a longitudinal slot or aperture cut into the anterior portion of the tibia and the talus, thereby achieving a desired ankle fusion.

BACKGROUND OF THE INVENTION

The ankle joint is one of the most commonly injured joint in the human body, and it may be injured in any one of a number of different ways. In many cases after an ankle injury the ankle joint can become arthritic, deformed or endure other systematic diseases and related issues.

Currently the typical prior art surgical procedures performed to treat ankle arthritis are ankle fusions and ankle replacement ("arthroplasty"). Arthroplasty has not yet achieved the success rates or acceptance like knee and hip replacement, which make ankle fusion the current procedure of choice for many patients.

The typical prior art procedures used to fixate an ankle joint (i.e. to perform an ankle fusion) do not always result in an optimal fused joint. One such prior art method is placing a plate tangentially on the outside of the tibia and the talus and driving multiple screws into both the tibia and the talus, thereby securing the plate to both bones and thereby fixating the ankle. Placing the plate on the front of the ankle joint (the tibia and the talus) normally secures the plate in a position relative to the fracture that the plate but not necessarily the fracture is in a state of compression. In many cases wherein the plate is in compression, the plate does not optimally secure the fracture as the forces on the bone and plate combination may tend to place undesirable directional forces in the bone around the fracture.

A second prior art method is one wherein multiple metal screws and/or nails which are screwed or driven into both bones, thereby penetrating and securing both the tibia and the talus. This approach leads to a range of variable results, some of which are undesirable from multiple perspectives. In many cases the nails utilized go through the bottom of the heel and are completely within the bone. This may result in the ankle joint and the subtalar joints being fused as well as requiring an incision on the heel, the side and on the front of the ankle thereby creating a very stirr limb.

It is an object of embodiments of this invention to provide a bone fusion system and method that may be intramedullary and provide the stabilization during bone healing without adversely affecting other surrounding joints.

It is a further object of this invention to provide a stronger plate and support system which may be inserted with minimal soft tissue and bone damage as part of the insertion process.

It is an object of embodiments of this invention to provide a transcortical bone fusion system which can be adapted not only to ankles, but to other joints desired to be fused, which provides an improved fusion generally internal to the tibia and talus in the ankle fusion application.

An advantage of embodiments of cutting small bone cuts in the tibia and talus and then inserting a small plate longitudinally oriented, which tends to maximize the strength of the plate in the application and is very low profile when compared to other prior art methods (especially those using plates mounted tangentially to the outer surface of the bones).

Other objects, features, and advantages of this invention will appear from the specification, claims, and accompanying drawings which form a part hereof. In carrying out the objects of this invention, it is to be understood that its essential features are susceptible to change in design and structural arrangement, with only one practical and preferred embodiment being illustrated in the accompanying drawings, as required.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

Figure 1:
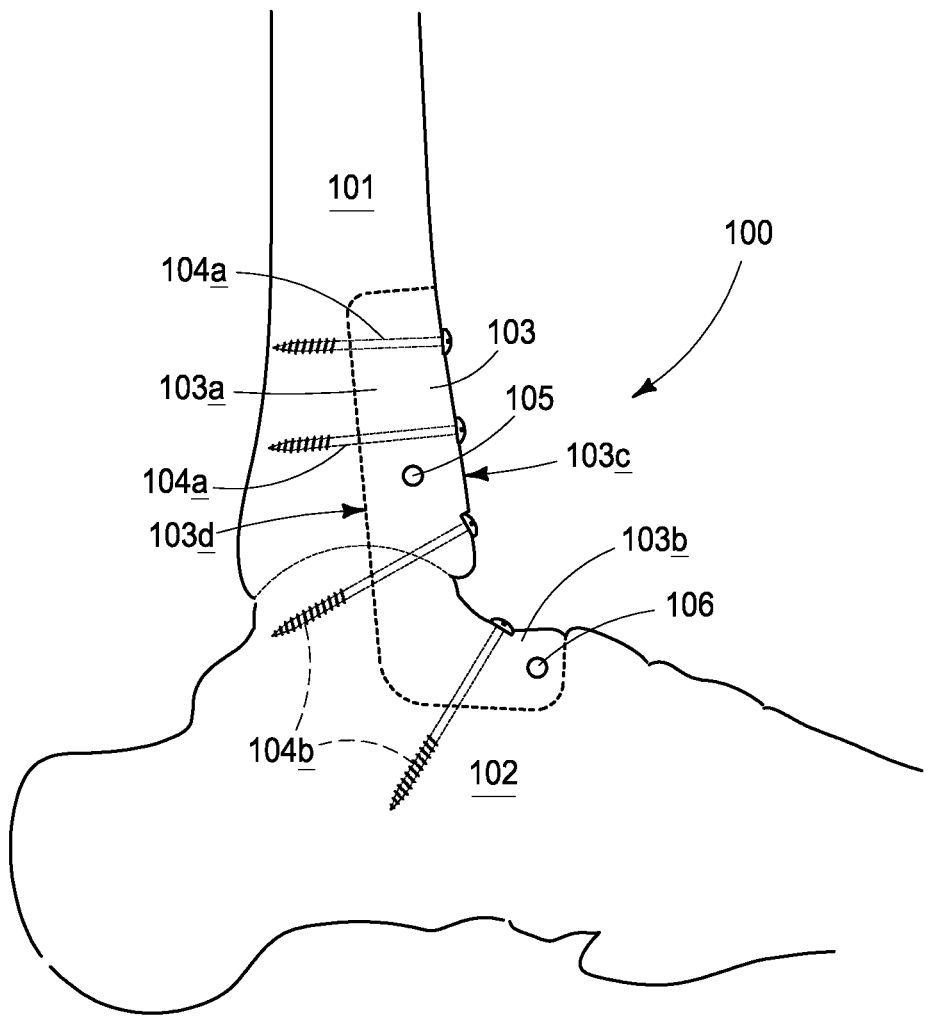
FIG. 1 is a side elevation view of an ankle joint showing an example of an embodiment of this invention inserted therein.

Many of the fastening, connection, manufacturing and other means and components utilized in this invention are widely known and used in the field of the invention described, and their exact nature or type is not necessary for an understanding and use of the invention by a person skilled in the art or science; therefore, they will not be discussed in significant detail. Furthermore, the various components shown or described herein for any specific application of this invention can be varied or altered as anticipated by this invention and the practice of a specific application or embodiment of any element may already be widely known or used in the art or by persons skilled in the art or science; therefore, each will not be discussed in significant detail.

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

It should be noted that while an ankle fusion is used to describe an example of an embodiment of the invention, this fusion system is not limited to any one particular bone joint combination, but instead may be applied to any one of a number of different joints.

In the ankle fusion example, the proposed ankle plate may be placed through a small bone cut made in the tibia and the talus. The cut aperture would be tailored to accommodate the transcortical plate to be inserted and would be more of a slot shape longitudinally oriented cut. It may be preferred in some embodiments of this invention and in practicing some embodiments of this invention, to include a cutting jig as a guide for a surgeon making the cut. In the embodiment in which a cutting jig is used, the jig may for example be fixed to and across the patient's ankle joint with a linear or arcuate slot which may be used to guide a bone saw to cut the desired slot into the tibia and the talus.

Once the slot or aperture is cut into the first bone and second bone generally contiguous, then the fixation plate may be inserted into each of the bones and necessarily across the joint between the bones. Once properly inserted and located, fasteners such as screws or nails may be utilized medially and/or transversely to fixate the plate to each of the bones. It should be noted that a plate inserted longitudinally as such and oriented as shown in the drawings, maximizes the strength of the plate much like an I-beam maximizes the strength of the component, and would be very low profile within the patient's bones (or completely intramedullary in some embodiments).

FIG. 1 is a side elevation view of an ankle joint showing an example of an embodiment of this invention inserted therein. FIG. 1 illustrates the tibia bone 101, the talus bone 102 and the transcortical or fusion plate 103 implanted within the tibia 101 and the talus 102. FIG. 1 also illustrates transverse apertures, namely a transverse tibia aperture 105 and transverse talus aperture 106, through which fasteners such as screws may be driven to secure the transcortical plate 103 to each of the bones, namely the tibia 101 and talus 102.

FIG. 1 shows four medially oriented screws, namely a first set 104a of tibia bone screws intended for fastening the transcortical plate to the tibia 101 and which may generally be perpendicular to the tibia. The first set 104a of screws are penetrating through the tibia screw apertures (shown as items 110a in FIG. 2) in the transcortical plate 103 and driven into the tibia 101. The second set 104b of talus screws on the other hand are utilized in fastening the transcortical plate 103 to the talus 102 and are angled downwardly at an angle to penetrate the talus screw apertures 110b in the transcortical plate 103 and then fasten into the talus 102. It should be noted that when the term downwardly is used herein in connection with the angle of the talus screws, it means at a downward angle regardless of the magnitude of the angle.

In some embodiments of this invention and as described elsewhere herein, the first set 104a of tibia fasteners are first affixed to the tibia 101, and thereafter the second set 104b of fasteners, namely the talus fasteners 104b, are affixed to the talus 102. By following this sequence the fastening of the second set 104b of screws may be utilized to pull the talus closer to and into compression contact with the lower portion of the tibia 101. It is desirable to compress the fusion site in some applications to better facilitate the objectives of the surgical implant.

FIG. 1 further illustrates a top portion 103a of the transcortical plate 103, the top portion 103a being inserted and secured into the tibia 101 in this example of the invention, and the bottom portion 103b being inserted into an aperture cut in the talus 102 of the patient. The transcortical or fusion plate 103 shown in FIG. 1 further shows an internal edge 103d and an external edge 103c.

It will be noted that while four medial and two transverse screw apertures are shown in transcortical plate 103, this invention is not limited to any particular number of screws or screw apertures but would apply to any one of a number of different combinations thereof, depending on the desired results in the particular application of the invention.

Figure 2:
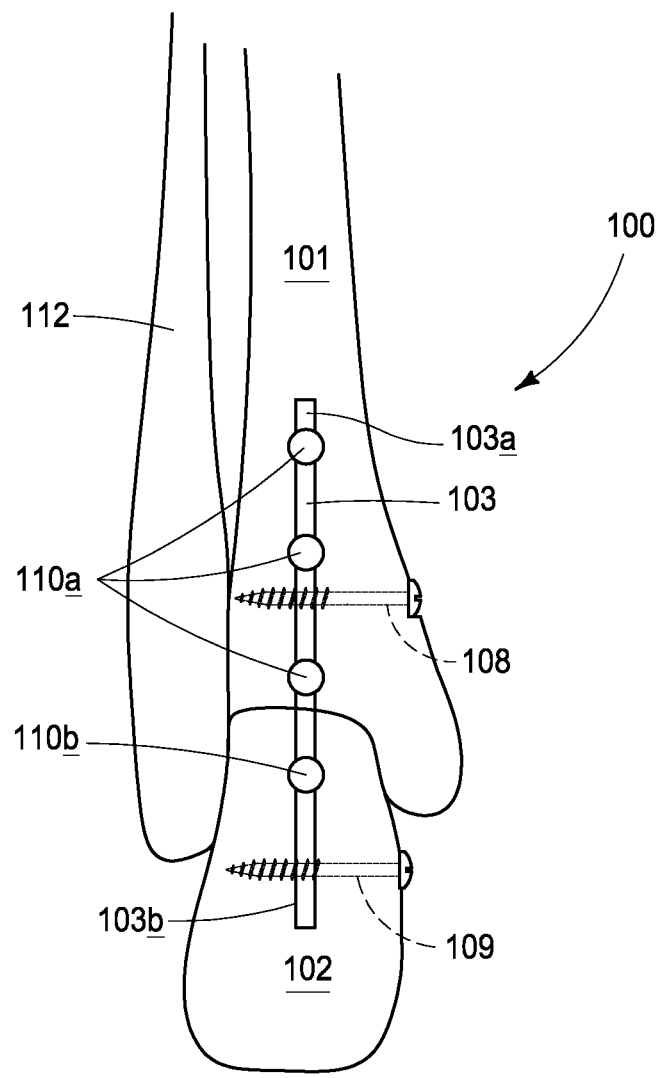
FIG. 2 is an end elevation view of the example of the embodiment of the invention illustrated in FIG. 1.

FIG. 2 is an end elevation view of the example of the embodiment of the invention 100 illustrated in FIG. 1 (only without the fasteners or screws therein), showing the tibia 101, the talus 102 and the fibula 112. FIG. 2 illustrates transcortical plate 103 with its top portion 103a and bottom portion 103b, medial screw apertures 110 (tibia screw apertures 110a and talus screw apertures 110b), transverse tibia screw 108 and transverse talus screw 109.

It should be noted that after the plate insertion into the tibia 101 and the talus 102, is preferable to first insert, drive or secure the tibia fasteners (such as screws 104a shown in FIG. 1) through tibia screw apertures 110a and into the tibia 101. Thereafter the lower talus screws 104 (shown in FIG. 1) may be inserted, driven or secured through talus screw apertures 110b and into the talus 102 so that when the talus screws are driven in the talus and secured, the joint is thereby more desirably compressed together as the fixation is taking place. It is preferable to thereafter insert, drive or secure the transverse fasteners, namely the transverse tibia screw 108 and the transverse talus screw 109, into the tibia 101 and talus 102 respectively.

It should also be noted that embodiments of the transcortical plate 103 fusion system result in the plate 103 and screws being wholly within the bones into which they are inserted and fastened, which may lead to a stronger fused joint in many embodiments of this invention.

Figure 3:
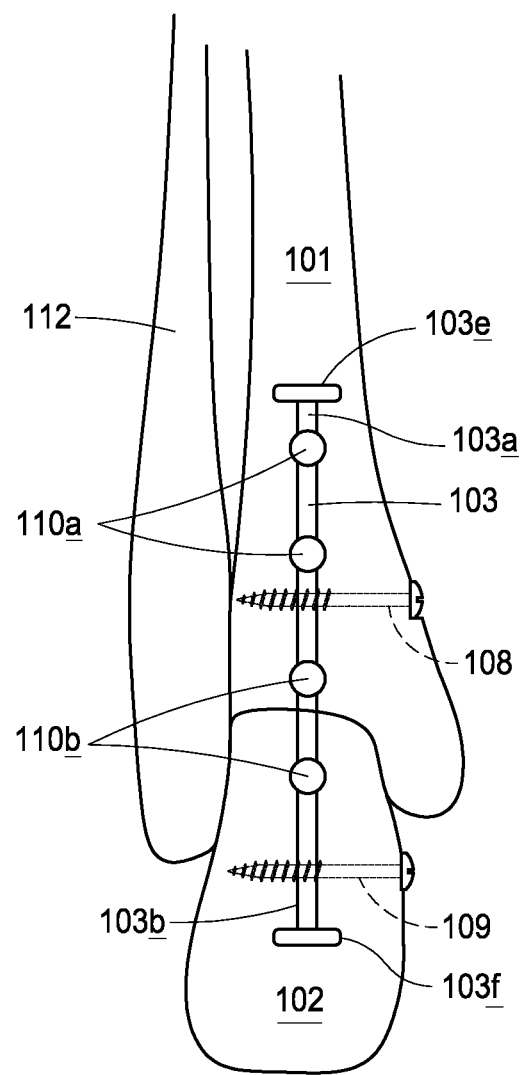
FIG. 3 is an end elevation view of an example of an embodiment of the invention as illustrated in FIG. 2, only with a flange at the top and/or bottom of the plate.

FIG. 3 is an end elevation view of an example of an embodiment of the invention as illustrated in FIG. 2, only with a first flange 103e at the top of the plate 103, and with a second flange 103f at the bottom of the plate 103. It should be noted that while a first flange 103e and a second flange 103f are shown, embodiments of this invention may include one or the other, or both flanges, all within the scope of this invention. All like numbered items from FIG. 2 are described in connection with FIG. 2 and will not be repeated here.

It should also be noted that while more typically configured flanges are shown in FIG. 3, it may be desirable (and is part of embodiments of this invention) to modify the configuration of the flange for ease of insertion in some applications, or to achieve different surface area objectives, again dependent on the application. For example a more rounded or arcuate surface area may be provided at the end of the plate (elliptical, circular or other) for desired strength or bone interaction objectives in a particular application or surgery.

Figure 4:
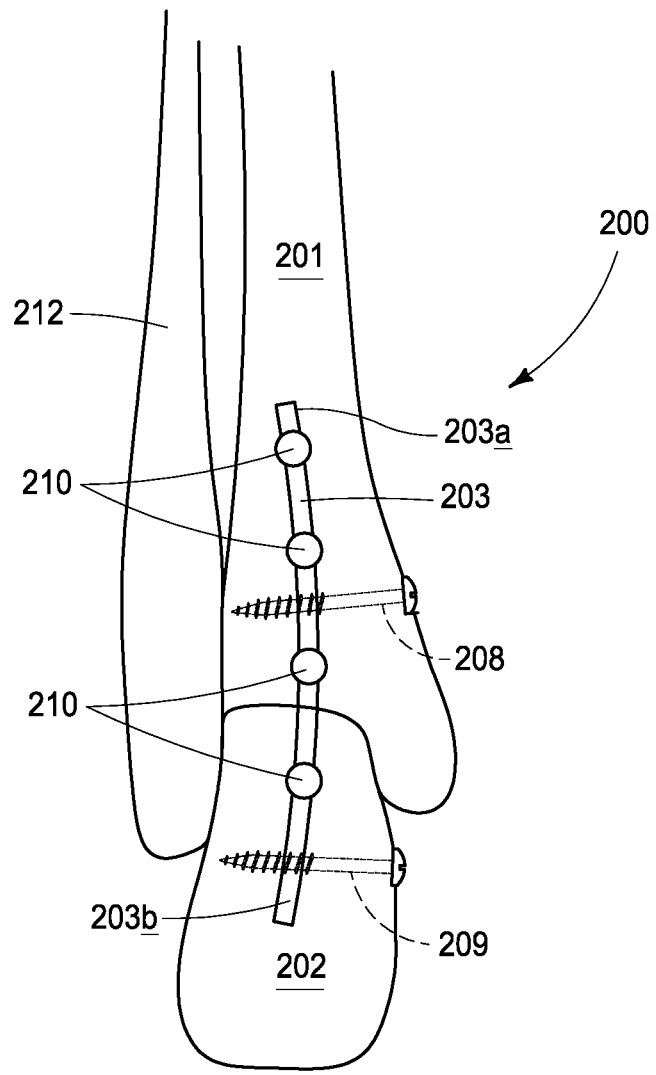
FIG. 4 is an end elevation view of another example of an embodiment of the invention with a plate defining an arcuate configuration.

FIG. 4 is an end elevation view of another example of an embodiment of the invention 200, only wherein the transcortical plate 203 is shown in a nonlinear configuration, namely in an arcuate configuration. FIG. 4 illustrates the tibia 201, the talus 202 and the fibula 212. FIG. 4 illustrates transcortical plate 203 with its top portion 203a and bottom portion 203b, medial screw apertures 210 and transverse screws 208.

Figure 5:
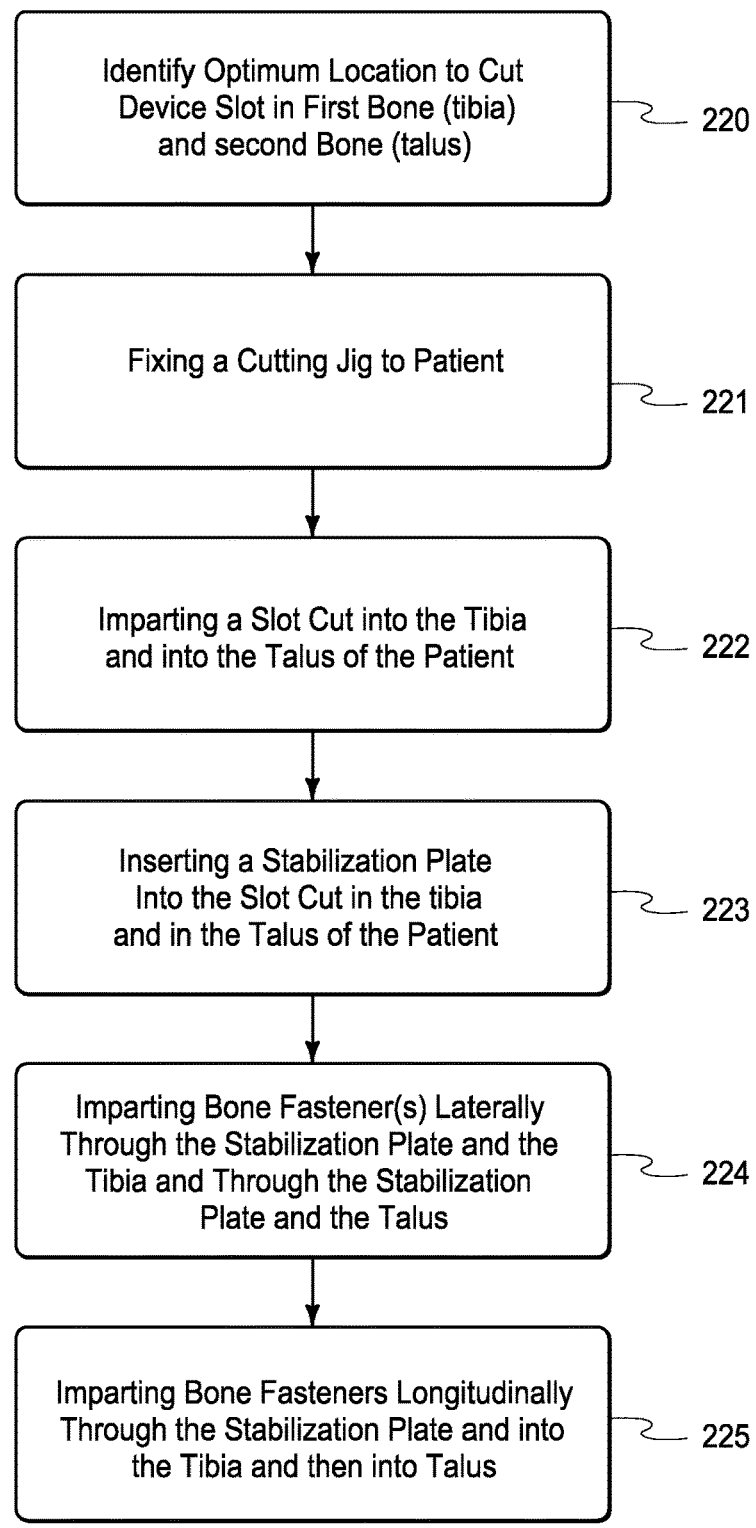
FIG. 5 is a flow chart of an example of a method practicing an embodiment of this invention.

FIG. 5 is a flow chart of an example of a method practicing an embodiment of this invention, generally showing the steps described below. At step 220 the optimum location is identified to cut a slot or aperture in the patient's tibia (first bone) and talus (second bone), such that the slot or aperture is configured to receive the transcortical plate.

At the next step 221, a cutting jig is secured or fixed to the patient to provide a jig pattern for the desired cut in the slot in first bone (tibia) and second bone (talus). Once the jig is affixed to the patient, at step 222 a slot is cut into the tibia and into the talus of the patient such that the slot or aperture is configured to receive the desired or selected transcortical plate.

Once the slot or plate aperture is cut and configured, at step 223 a stabilization, transcortical or fusion plate is then inserted into the slot or aperture in the tibia and in the talus of the patient. Once the transcortical plate is inserted there are various options for fastening or securing the plate to the tibia and to the talus at step 224. In some embodiments of this invention, it is preferred to first impart the medial tibia screws through the plate longitudinally, first into the tibia to secure it and then into the talus. In sequencing it this way, the insertion or driving of the fasteners (screws in the embodiment shown) will tend to draw or pull the talus upward toward the tibia so that the joint is brought together in bias or compression as the fastener (screw) is secured into the talus.

At that point after the plate is medially or longitudinally affixed to the tibia and to the talus (and the joint drawn together in the process), the tibia and talus lateral or transverse fasteners (such as but not limited to screws) may be inserted at step 225, through the transcortical plate and the tibia and then through the transcortical plate and in the talus.

As will be appreciated by those of reasonable skill in the art, there are numerous embodiments to this invention, and variations of elements and components which may be used, all within the scope of this invention. In one embodiment for example, providing a method for fusing an ankle joint including a tibia bone and a talus bone comprising: providing a transcortical ankle fusion plate sized and configured for insertion into the medial side of a tibia bone and in a talus bone, the fusion plate comprising: one or more tibia fastener apertures configured to receive a fastener there-through and direct the fastener into the tibia; one or more talus fastener apertures configured to receive a fastener there-through and direct the fastener downwardly into the tibia; a tibia lateral fastener aperture through the fusion plate at a location at which the fusion plate will be inserted in the tibia; and a talus lateral fastener aperture through the fusion plate at a location at which the fusion plate will be inserted in the talus; cutting a slot into the tibia bone and into the talus bone of the patient such that the slot in the tibia bone and in the talus bone is configured to receive the fusion plate; inserting the fusion plate into the slot in the tibia bone and in the talus bone; inserting tibia fasteners through the one or more tibia fastener apertures and securing the tibia fasteners into the tibia; and inserting talus fasteners downwardly through the one or more talus fastener apertures and into the talus, such that the inserting or fastening of the talus fasteners into the talus pulls the talus toward the tibia thereby imposing a compression between the talus and the tibia.

Additional and further steps to those disclosed in the preceding paragraph, the method described for fusing an ankle joint may further comprise: inserting a lateral tibia fastener through the tibia lateral fastener aperture in the fusion plate and into the tibia; further inserting a lateral talus fastener through the talus lateral fastener aperture in the fusion plate and into the talus; further wherein the fusion plate is wholly inserted into the slot in the tibia bone and in the talus bone; further after the fusion plate is provided, securing a cutting jig to the patient to provide a cutting pattern for the desired cut in the slot in the tibia and in the talus; and/or still further wherein the first set and second set of fasteners are bone screws.

In a further embodiment of the invention, an apparatus embodiment, a transcortical ankle fusion plate may be provided which is sized and configured for insertion into the medial side of a tibia bone and into an adjacent talus bone, the fusion plate including: one or more tibia fastener apertures configured to receive a fastener there-through and direct the fastener into the tibia; one or more talus fastener apertures configured to receive a fastener there-through and direct the fastener downwardly into the tibia; a tibia lateral fastener aperture through the fusion plate at a location at which the fusion plate will be inserted in the tibia; and a talus lateral fastener aperture through the fusion plate at a location at which the fusion plate will be inserted in the talus.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method for fusing an ankle joint including a tibia bone and a talus bone comprising:
   providing a transcortical ankle fusion plate sized and configured for insertion into the medial side of a tibia bone and in a talus bone, the fusion plate comprising:
      an internal edge, an external edge, opposing side surfaces between the internal edge and the external edge;
      one or more tibia fastener apertures through the fusion plate and configured to receive a fastener there-through and direct the fastener into the tibia;
      one or more talus fastener apertures configured to receive a fastener directed toward the tibia;
      a tibia lateral fastener aperture through the fusion plate at a location at which the fusion plate will be inserted in the tibia bone; and
      a talus lateral fastener aperture through the fusion plate at a location at which the fusion plate will be inserted in the talus bone;
   cutting a slot into the tibia bone and into the talus bone of the patient such that the slot in the tibia bone and in the talus bone is configured to receive internal edge of the fusion plate;
   inserting the internal edge of the top portion and bottom portion of the fusion plate into the slot in the tibia bone and in the talus bone respectively, and inserting the fusion plate into the slot until the external edge of the fusion plate is at a desired location relative to the tibia bone and talus bone;
   inserting tibia fasteners through the one or more tibia fastener apertures and securing the tibia fasteners into the tibia; and
   inserting talus fasteners downwardly through the one or more talus fastener apertures and into the talus bone, such that the inserting the talus fasteners into the talus bone pulls the talus bone toward the tibia bone, thereby imposing a compression between the talus bone and the tibia bone.

2. A method for fusing an ankle joint as recited in claim 1, and further inserting a lateral tibia fastener through the tibia lateral fastener aperture in the fusion plate and into the tibia bone.

3. A method for fusing an ankle joint as recited in claim 1, and further inserting a lateral talus fastener through the talus lateral fastener aperture in the fusion plate and into the talus bone.

4. A method for fusing an ankle joint as recited in claim 1, and further wherein the fusion plate is wholly inserted into the slot in the tibia bone and in the talus bone.

5. A method for fusing an ankle joint as recited in claim 1, and further after the fusion plate is provided, securing a cutting jig to the patient to provide a cutting pattern for the desired cut in the slot in the tibia bone and in the talus bone.

6. A method for fusing an ankle joint as recited in claim 1, and wherein the first set and second set of fasteners are bone screws.

7. A method for fusing an ankle joint including a tibia bone and a talus bone as recited in claim 1, and further wherein the inserting the talus fasteners into the talus bone pulls the talus bone toward the tibia bone, thereby imposing a compression on a fusion site on the tibia bone or the talus bone.

* * * * *